United States Patent
Konno et al.

(10) Patent No.: US 10,473,618 B2
(45) Date of Patent: Nov. 12, 2019

(54) RESIDUAL CHLORINE MEASURING APPARATUS AND METHOD OF MEASURING RESIDUAL CHLORINE

(71) Applicant: KURITA WATER INDUSTRIES LTD., Tokyo (JP)

(72) Inventors: Yuko Konno, Tokyo (JP); Hiromitsu Hachiya, Tokyo (JP)

(73) Assignee: KURITA WATER INDUSTRIES LTD., Tokyo (JP)

(*) Notice: Subject to any disclaimer, the term of this patent is extended or adjusted under 35 U.S.C. 154(b) by 72 days.

(21) Appl. No.: 15/258,817

(22) Filed: Sep. 7, 2016

(65) Prior Publication Data

US 2017/0089860 A1 Mar. 30, 2017

(30) Foreign Application Priority Data

Sep. 10, 2015 (JP) .................... 2015-178328

(51) Int. Cl.
*G01N 27/416* (2006.01)
*G01N 27/30* (2006.01)

(52) U.S. Cl.
CPC ......... *G01N 27/4168* (2013.01); *G01N 27/30* (2013.01)

(58) Field of Classification Search
CPC ... G01N 27/416; G01N 27/4168; G01N 27/30
USPC ........ 204/174, 400–412, 414–420, 430–435; 205/778.5–780, 789–789.5, 794.5
See application file for complete search history.

(56) References Cited

U.S. PATENT DOCUMENTS

2012/0216605 A1* 8/2012 Silveri ............... G01N 27/08
73/61.41

FOREIGN PATENT DOCUMENTS

| JP | H10-111274 A | 4/1998 |
| JP | H10-185871 A | 7/1998 |
| JP | H11-333460 A | 12/1999 |
| JP | 2001-091495 A | 4/2001 |
| JP | 2001-174436 A | 6/2001 |
| JP | 2005062133 A | 3/2005 |
| JP | 2006-194751 A | 7/2006 |
| JP | 3832399 B2 | 10/2006 |
| JP | 2008-058025 A | 3/2008 |
| JP | 2015-034741 A | 2/2015 |

OTHER PUBLICATIONS

Office Action, Japanese Patent Application No. 2015-178328, dated May 28, 2019.

* cited by examiner

*Primary Examiner* — Matthew T Martin
(74) *Attorney, Agent, or Firm* — Marshall, Gerstein & Borun LLP (57) ABSTRACT

A residual chlorine measuring apparatus includes: a detection electrode that is immersed in a sample solution, the detection electrode being made of gold or platinum; a counter electrode that is immersed in the sample solution, the counter electrode being made of silver/silver chloride; a voltage applying device that applies an applied voltage between the detection electrode and the counter electrode; an ammeter that measures an oxidation-reduction current flowing between the detection electrode and the counter electrode; and an arithmetic controller that controls the voltage applying device and acquires the oxidation-reduction current measured by the ammeter.

4 Claims, 4 Drawing Sheets

RESIDUAL CHLORINE MEASURING APPARATUS AND METHOD OF MEASURING RESIDUAL CHLORINE

CROSS REFERENCE TO RELATED APPLICATIONS

Priority is claimed on Japanese Patent Application No. 2015-178328, filed on Sep. 10, 2015, the content of which is incorporated herein by reference.

BACKGROUND OF THE INVENTION

Field of the Invention

The present invention relates to residual chlorine measuring apparatus and a method of measuring residual chlorine. To be more specific, the present invention relates to a residual chlorine measuring apparatus and a method of measuring residual chlorine that are suitable for measuring residual chlorine in water in which a stabilizing agent that reduces degradation of a chlorine-based oxidizing agent is added to a chlorine-based oxidizing agent.

Description of Related Art

Residual chlorine is the effective chlorine having a disinfectant action, which remains in water after chlorination, and is classified into free residual chlorine such as hypochlorous acid and combined residual chlorine such as chloramines or chlorosulfamates. Both free residual chlorine and combined residual chlorine have a bactericidal capacity due to oxidation.

A halogen-based oxidizing agent such as a hypochlorite generates free residual chlorine and has a high bactericidal capacity. However, the halogen-based oxidizing agent is likely to be degraded by an ultraviolet ray and thus has low stability in water. In addition, a problem arises in that the halogen-based oxidizing agent has high oxidative power, and thus has high corrosivity.

Hence, in order to reduce the degradation of a chlorine-based oxidizing agent such as a hypochlorite, a technique in which a sulfamic acid salt or the like is added as a stabilizing agent is known. When a sulfamic acid salt is added to a hypochlorite, an N-monochlorosulfamate or an N, N-dichlorosulfamate is formed. In other words, combined residual chlorine is produced.

Combined residual chlorine has a low oxidative power; however, reaction of the combined residual chlorine with water makes it possible to produce free residual chlorine for a long period of time.

In addition, in order to further stabilize a chlorine-based oxidizing agent, a technique in which sulfamic acid or a sulfamic acid salt, and an azole-based compound such as benzotriazole are added to a chlorine-based oxidizing agent is known (Japanese Patent No.3832399). The benzotriazole or the like is used to achieve corrosion prevention or the like of a pipe or the like, and thus, chlorination target water contains benzotriazole in some cases.

In chlorination, it is important to measure a residual chlorine concentration and to adjust an amount of the oxidizing agent used. As a method of measuring the residual chlorine concentration, an o-tolidine colorimetric method (OT method) or a diethyl-p-phenylenediamine colorimetric method (DPD method) is known. In addition, the residual chlorine concentration measurement may be performed by a polarographic method (for example, Japanese Unexamined Patent Application, First Publication No. 2005-62133).

The residual chlorine concentration measurement performed by a polarographic method is a method suitable for continual measurement or automation.

However, according to findings of the inventors, in a case of water in which benzotriazole or the like is contained, a sufficient current output is not acquired even when the measurement of the residual chlorine concentration is performed by a polarographic method.

According to research of the inventors, in a case of water in which benzotriazole or the like is contained, it is found that a surface of a detection electrode is instantaneously covered with a coating of benzotriazole or the like, which inhibits the detection electrode from reacting with the residual chlorine.

In consideration of the circumstances described above, an object of the present invention is to provide a residual chlorine measuring apparatus and a method of measuring residual chlorine which use a polarographic method, in which it is possible to calculate a total residual chlorine concentration of water in which benzotriazole or the like is contained.

SUMMARY OF THE INVENTION

In order to achieve the object described above, the present invention employs the following configurations.

According to a first aspect of the present invention, a residual chlorine measuring apparatus includes: a detection electrode that is immersed in a sample solution, the detection electrode being made of gold or platinum; a counter electrode that is immersed in the sample solution, the counter electrode being made of silver/silver chloride; a voltage applying device that applies an applied voltage between the detection electrode and the counter electrode; an ammeter that measures an oxidation-reduction current flowing between the detection electrode and the counter electrode; and an arithmetic controller that controls the voltage applying device and acquires the oxidation-reduction current measured by the ammeter, in which the arithmetic controller is configured to perform a step A1 of applying an applied voltage $V_{a1}$ in a range of −0.5 to −2.0 V between the detection electrode and the counter electrode for a period of time $T_{a1}$, a step A2 of applying an applied voltage $V_{a2}$ in a range of 0.5 to 2.0 V between the detection electrode and the counter electrode for a period of time $T_{a2}$, a step A3 of applying an applied voltage $V_{a3}$ in a range of −0.5 to −2.0 V, after the step A2, between the detection electrode and the counter electrode for a period of time $T_{a3}$, a step B1 of applying an applied voltage $V_{b1}$ in a range of 0.5 to 2.0 V between the detection electrode and the counter electrode for a period of time $T_{b1}$ that satisfies a condition of $T_{b1} \leq T_{a2}$, a step B2 of applying an applied voltage $V_{b2}$ that satisfies conditions of $V_{b2}=0$ to −2.0 V and $V_{b2} \neq 0$ V, after the step B1, between the detection electrode and the counter electrode for a period of time $T_{b2}$ that satisfies conditions of $T_{b2} \leq T_{a1}$ and $T_{b2} \leq T_{a3}$, and a step B3 of applying an applied voltage $V_{b3}$ in a range of −0.5 to 0.2 V, after the step B2, between the detection electrode and the counter electrode while a voltage is maintained to be constant, the arithmetic controller is configured to control the voltage applying device such that the voltage applying device performs the step A2 and the step A3 one or more times after the step A1 and performs the step B1 to the step B3 one or more times after performing the step A2 and the step A3 one or more times, and the arithmetic controller is configured to acquire an oxidation-reduction current obtained by the ammeter in the step B3 as a measurement current, and to calculate a total residual chlorine concentration of the sample solution, according to the measurement current.

The period of time $T_{a1}$ may be 0.1 to 3.0 seconds, the period of time $T_{a2}$ may be 0.1 to 3.0 seconds, the period of time $T_{a3}$ may be 0.1 to 3.0 seconds, the period of time $T_{b1}$ may be 0.01 to 1.0 second, and the period of time $T_{b2}$ may be 0.01 to 1.0 second.

According to a second aspect of the present invention, a method of measuring residual chlorine includes: preparing a sample solution, a detection electrode that is immersed in the sample solution, and a counter electrode that is immersed in the sample solution, the detection electrode being made of gold or platinum, the counter electrode being made of silver/silver chloride; a step A1 of applying an applied voltage $V_{a1}$ in a range of −0.5 to −2.0 V between the detection electrode and the counter electrode for a period of time $T_{a1}$; a step A2 of applying an applied voltage $V_{a1}$ in a range of 0.5 to 2.0 V between the detection electrode and the counter electrode for a period of time $T_{a2}$; a step A3 of applying an applied voltage $V_{a3}$ in a range of −0.5 to −2.0 V, after the step A2, between the detection electrode and the counter electrode for a period of time $T_{a3}$; a step B1 of applying an applied voltage $V_{b1}$ in a range of 0.5 to 2.0 V between the detection electrode and the counter electrode for a period of time $T_{b1}$ that satisfies a condition of $T_{b1} \leq T_{a2}$; a step B2 of applying an applied voltage $V_{b2}$ that satisfies conditions of Vb2=0 to −2.0 V and $V_{b2} \neq 0$ V, after the step B1, between the detection electrode and the counter electrode for a period of time $T_{b2}$ that satisfies conditions of $T_{b2} \leq T_{a1}$ and $T_{b2} \leq T_{a3}$; and a step B3 of applying an applied voltage $V_{b3}$ in a range of −0.5 to 0.2 V, after the step B2, between the detection electrode and the counter electrode while a voltage is maintained to be constant, performing the step A2 and the step A3 one or more times after the step A1, performing the step B1 to the step B3 one or more times after performing the step A2 and the step A3 one or more times, and calculating a total residual chlorine concentration of the sample solution, according to a measurement current, the measurement current being an oxidation-reduction current obtained in the step B3, which flows between the detection electrode and the counter electrode.

The period of time $T_{a1}$ may be 0.1 to 3.0 seconds, the period of time $T_{a2}$ may be 0.1 to 3.0 seconds, the period of time $T_{a3}$ may be 0.1 to 3.0 seconds, the period of time $T_{b1}$ may be 0.01 to 1.0 second, and the period of time $T_{b2}$ may be 0.01 to 1.0 second.

The sample solution may be water containing one selected from the group consisting of hypochlorous acid and a hypochlorite, and one selected from the group consisting of sulfamic acid and a sulfamic acid salt.

The sample solution may contain one selected from the group consisting of benzotriazole and benzotriazole salt.

In the residual chlorine measuring apparatus and the method of measuring residual chlorine according to the aspects described above, it is possible to calculate the total residual chlorine concentration of water in which benzotriazole or the like is contained.

DETAILED DESCRIPTION OF THE PREFERRED EMBODIMENTS

<Configuration of Residual Chlorine Measuring Apparatus>

Figure 1:
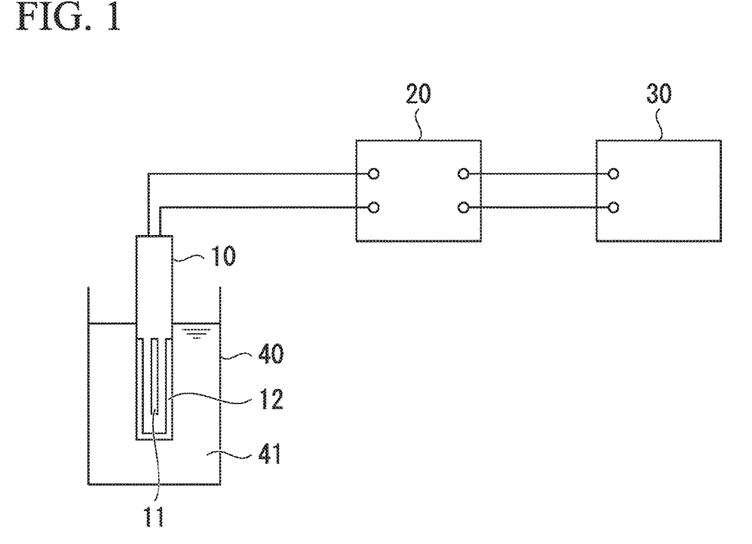
FIG. 1 is a diagram showing a schematic configuration of a residual chlorine measuring apparatus according to a first embodiment of the present invention.

As shown in FIG. 1, a residual chlorine measuring apparatus according to a first embodiment of the present invention is configured to include a sensor 10, a potentiostat 20, and an arithmetic controller 30.

The sensor 10 has a detection electrode 11 and a counter electrode 12 which are immersed in a sample solution 41 contained in a sample solution container 40. The detection electrode 11 is made of gold or platinum. In addition, the counter electrode 12 is made of silver/silver chloride.

An oxidation-reduction current that is measured in the embodiment is a diffusion current which flows when a reduction target substance is carried to a surface of a detection electrode only through natural diffusion due to a concentration gradient in a layer referred to as a diffusion layer and the reduction target substance carried to the surface of the detection electrode is reduced on the surface of the detection electrode.

As the sensor 10, it is possible to employ a known appropriate structure. In other words, it is possible to appropriately select a specific structure or arrangement of the detection electrode 11 and the counter electrode 12 in the sensor 10. In addition, the sensor 10 may have a structure in which a portion having the detection electrode 11 is separated from a portion having the counter electrode 12. In addition, the sample solution container 40 can be appropriately changed to a flow cell or the like.

The sensor 10 may further have a reference electrode, in addition to the detection electrode 11 and the counter electrode 12. Note that, in a case where the sensor does not have the reference electrode, the counter electrode 12 serves as the reference electrode.

It is preferable that the sensor 10 further has a temperature sensor for temperature correction. The temperature correction means conversion to an oxidation-reduction current at a reference temperature (for example, 25° C.), in consideration of temperature dependence of measurement of the oxidation-reduction current.

The potentiostat 20 includes a voltage applying device that applies a predetermined applied voltage between the detection electrode 11 and the counter electrode 12, and an ammeter that measures the oxidation-reduction current flowing between the detection electrode 11 and the counter electrode 12 when the applied voltage is applied by the voltage applying device.

The arithmetic controller 30 controls the predetermined applied voltage that is applied between the detection electrode 11 and the counter electrode 12 by the potentiostat 20.

The arithmetic controller 30 is configured to control the voltage applying device of the potentiostat 20 and to acquire the oxidation-reduction current measured by the ammeter of the potentiostat 20 such that the residual chlorine measuring apparatus according to the embodiment executes a method of measuring residual chlorine according to a second embodiment of the present invention, which will be described below.

In other words, under control by the arithmetic controller 30, the residual chlorine measuring apparatus according to the embodiment is configured to perform a preprocessing step which will be described below and measurement steps following the preprocessing step. The arithmetic controller 30 is configured to acquire, as a measuring current, the oxidation-reduction current that is obtained at a specific timing of the measurement steps, and to calculate a total residual chlorine concentration of the sample solution 41, according to the acquired measuring current.

<Method of Measuring Residual Chlorine>

The method of measuring residual chlorine according to the second embodiment of the present invention is a method in which predetermined applied voltages are applied in order between the gold or platinum detection electrode immersed in the sample solution and to the silver/silver chloride counter electrode, and the total residual chlorine concentration of the sample solution is calculated using the oxidation-reduction current flowing between the detection electrode and the counter electrode.

The predetermined applied voltage is set to perform the preprocessing step, to be described below, and the measurement steps, to be described below, following the preprocessing step. The method of measuring residual chlorine according to the embodiment is configured to acquire, as the measuring current, the oxidation-reduction current in step B3 of the measurement steps and to calculate the total residual chlorine concentration of the sample solution, according to the measuring current.

[Sample Solution]

In the method of measuring residual chlorine according to the embodiment, in a case where the sample solution is water containing hypochlorous acid or a hypochlorite, and sulfamic acid or a sulfamic acid salt, the total residual chlorine concentration is calculated. In addition, also in a case where the sample solution further contains benzotriazole or a benzotriazole salt, in addition to hypochlorous acid or a hypochlorite, and sulfamic acid or a sulfamate, the total residual chlorine concentration is calculated.

Examples of hypochlorite can include sodium hypochlorite, potassium hypochlorite, calcium hypochlorite, barium hypochlorite, and the like. One type of hypochlorous acid and a hypochlorite thereof may be contained or two or more types thereof may be contained.

Examples of a sulfamic acid salt (sulfamate) can include sodium sulfamate, potassium sulfamate, calcium sulfamate, strontium sulfamate, barium sulfamate, iron sulfamate, zinc sulfamate, and the like. One type of sulfamic acid and a sulfamic acid salt thereof may be contained or two or more types thereof may be contained.

For example, a hypochlorite ion and sulfamic acid reacts as in the following Expressions (1) and (2), an N-monochlorosulfamic acid ion or an N, N-dichlorosulfamic acid ion is formed such that an active substance of a chlorine-based oxidizing agent is stabilized.

$$HClO + H_2NSO_3^- \rightarrow HClNSO_3^- + H_2O \quad (1)$$

$$2HClO + H_2NSO_3^- \rightarrow Cl_2NSO_3^- + 2H_2O \quad (2)$$

Examples of the water containing hypochlorous acid or a hypochlorite, and sulfamic acid or a sulfamic acid salt include various types of water such as cooling water, pulp and paper process water, dust collecting water, scrubber water, or fountain.

Examples of a salt of benzotriazole (chemical name: 1,2,3-benzotriazole) (benzotriazole salt) include 1,2,3-benzotriazole sodium salt, 1,2,3-benzotriazole potassium salt, and the like.

One type of benzotriazole or benzotriazole salt (hereinafter, benzotriazole and benzotriazole salt are collectively referred to as "benzotriazoles") may be contained or two or more types thereof may be contained.

Benzotriazoles may be added as a stabilizing agent of the hypochlorous acid or a hypochlorite, and may be added as a rust inhibitor or an anticorrosive of pipes or the like.

[Preprocessing Step]

The preprocessing step is a step of performing the following step A1 and then continually performing the following step A2 and step A3 one or more times.

Step A1: a step of applying an applied voltage $V_{a1}$ (here, $V_{a1}=-0.5$ to $-2.0$ V) for a period of time $T_{a1}$.

Step A2: a step of applying an applied voltage $V_{a2}$ (here, $V_{a2}=0.5$ to $2.0$ V) for a period of time $T_{a2}$.

Step A3: a step of applying an applied voltage $V_{a3}$ (here, $V_{a3}=-0.5$ to $-2.0$ V) for a period of time $T_{a1}$, continually after step A2.

The applied voltage $V_{a1}$ of step A1 is $-0.5$ to $-2.0$ V, preferably $-0.8$ to $-2.0$ V, and more preferably $-0.8$ to $-1.8$ V. The applied voltage $V_{a1}$ may be maintained to be constant during step A1 or may be changed in a predetermined range.

The application of the applied voltage $V_{a1}$ makes it possible to remove an oxide coating formed on the surface of the detection electrode in the measurement step or during storage. When an absolute value of the applied voltage $V_{a1}$ is too small, it is not possible to remove the oxide coating, and when the absolute value is too large, a problem arises in that the oxide coating is removed, then electrolysis occurs, and hydrogen gas or the like is generated.

The period of time $T_{a1}$, during which step A1 is performed, is preferably 0.1 to 3.0 seconds, more preferably 0.5 to 3.0 seconds, and still more preferably 0.8 to 2.0 seconds. When the period of time $T_{a1}$ is equal to or longer than the preferable lower limit value (0.1 seconds), the oxide coating formed on the surface of the detection electrode is likely to be removed. When the period of time $T_{a1}$ is equal to or shorter than the preferable upper limit value (3.0 seconds), the coating of benzotriazoles is unlikely to be formed.

Step A2 is continually performed after step A1 or step A3. The applied voltage $V_{a2}$ of step A2 is 0.5 to 2.0 V, preferably 0.8 to 2.0 V, and more preferably 0.8 to 1.5 V. The applied voltage $V_{a2}$ may be maintained to be constant during step A2 or may be changed in a predetermined range.

The application of the applied voltage $V_{a2}$ makes it possible to remove the coating of benzotriazoles formed on the surface of the detection electrode in step A1 or step A3. When an absolute value of the applied voltage $V_{a2}$ is too small, it is not possible to remove the coating of benzotriazoles, and when the absolute value is too large, an oxide coating is likely to be formed.

The period of time $T_{a2}$, during which step A2 is performed, is preferably 0.1 to 3.0 seconds, more preferably 0.1 to 2.0 seconds, and still more preferably 0.8 to 1.5 seconds. When the period of time $T_{a2}$ is equal to or longer than the preferable lower limit value (0.1 seconds), the coating of benzotriazoles is likely to be removed. When the period of time $T_{a2}$ is equal to or shorter than the preferable upper limit value (3.0 seconds), the oxide coating is unlikely to be formed again.

Step A3 is continually performed after step A2. The applied voltage $V_{a3}$ of step A3 is −0.5 to −2.0 V, preferably −0.8 to −2.0 V, and more preferably −0.8 to −1.5 V. The applied voltage $V_{a3}$ may be maintained to be constant during step A3 or may be changed in a predetermined range. In addition, the applied voltage $V_{a3}$ may be equal to the applied voltage $V_{a1}$ or may be different from the applied voltage $V_{a1}$. However, since the oxide coating is once removed in step A1, an absolute value of the applied voltage $V_{a3}$ is preferably equal to or smaller than the absolute value of the applied voltage $V_{a1}$.

The application of the applied voltage $V_{a3}$ makes it possible to remove the oxide coating formed on the surface of the detection electrode in step A2. When the absolute value of the applied voltage $V_{a3}$ is too small, it is not possible to remove the oxide coating, and, when the absolute value is too large, a problem arises in that the oxide coating is removed, then electrolysis occurs, and hydrogen gas or the like is generated.

The period of time $T_{a3}$, during which step A3 is performed, is preferably 0.1 to 3.0 seconds, more preferably 0.1 to 2.0 seconds, and still more preferably 0.5 to 1.5 seconds. When the period of time $T_{a3}$ is equal to or longer than the preferable lower limit value (0.1 seconds), the formed oxide coating is likely to be removed. When the period of time $T_{a3}$ is equal to or shorter than the preferable upper limit value (3.0 seconds), the coating of benzotriazoles is unlikely to be formed again. Since the oxide coating is once removed in step A1, it is preferable that the period of time $T_{a3}$ is equal to or shorter than the period of time $T_{a1}$.

In the preprocessing step, it is preferable that step A2 and step A3 are continually performed once to twice. The preprocessing step of a case where step A2 and step A3 are continually performed once is a step in which step A1, step A2, and step A3 are continually performed in this order. The preprocessing step of a case where step A2 and step A3 are continually performed twice is a step in which step A1, step A2, step A3, step A2, and step A3 are continually performed in this order.

As a result of study of the inventors, when the process starts from step A2 without performing step A1, it is found that a residual current is increased whenever measurement is repeatedly performed in the measurement step after step A2 and step A3 although step A2 and step A3 are repeatedly performed a plurality of times. In other words, first of all, it is found that there is a need to remove the oxide coating from the surface of the detection electrode.

[Measurement Step]

The measurement step is a step of performing the following steps B1 to B3 one or more times. Note that, since a range of an applied voltage $V_{b2}$ in step B2 partially overlaps a range of an applied voltage $V_{b3}$ in step B3, the applied voltage $V_{b2}$ may be equal to the applied voltage $V_{b3}$. In addition, the applied voltage $V_{b2}$ after step B2 may be equal to the applied voltage $V_{b3}$. In other words, a timing of transition from step B2 to step B3 may not be clear.

Step B1: a step of applying the applied voltage $V_{b1}$ (here, $V_{b1}$=0.5 to 2.0 V) for a period of time $T_{b1}$ (here, $T_{b1} \leq T_{a2}$).

Step B2: a step of applying the applied voltage $V_{b2}$ (here, $V_{b2}$=0 to −2.0 V and $V_{b2} \neq 0$ V) for a period of time $T_{b2}$ (here, $T_{b2} \leq T_{a1}$ and $T_{b2} \leq T_{a3}$) continually after step B1.

Step B3: a step of applying the constantly maintained applied voltage $V_{b3}$ (here, $V_{b3}$=−0.5 to 0.2 V) continually after step B2.

The applied voltage $V_{b1}$ of step B1 is 0.5 to 2.0 V, preferably 0.8 to 2.0 V, and more preferably 0.8 to 1.5 V. The applied voltage $V_{b1}$ may be maintained to be constant during step B1 or may be changed in a predetermined range. In addition, the applied voltage $V_{b1}$ may be equal to the applied voltage $V_{a2}$, or may be different from the applied voltage $V_{a2}$. However, since the oxide coating is removed in step A2 once, it is preferable that an absolute value of the applied voltage $V_{b1}$ is equal to or smaller than the absolute value of the applied voltage $V_{a2}$.

The application of the applied voltage $V_{b1}$ makes it possible to remove the coating of benzotriazoles formed on the surface of the detection electrode during step A3 last performed in the preprocessing process or until the previous measurement step. When the absolute value of the applied voltage $V_{b1}$ is too small, it is not possible to remove the layer of benzotriazoles from the surface of the detection electrode, and when the absolute value is too large, an oxide layer is likely to be formed.

The period of time $T_{b1}$, during which step B1 is performed, is equal to or shorter than the period of time $T_{a2}$, during which step A2 is performed. Since the coating of benzotriazoles is reliably removed in step A2, it is possible to remove the coating to the extent that the measurement of the oxidation-reduction current is performed in step B3 without difficulty even in a short time. In addition, this is because the oxide coating is likely to be formed when the period of time is long.

The period of time $T_{b1}$, during which step B1 is performed, is preferably 0.01 to 1.0 second, more preferably 0.05 to 1.0 second, and still more preferably 0.2 to 0.8 seconds.

Step B2 is continually performed after step B1. The applied voltage $V_{b2}$ of step B2 is 0 to −2.0 V, and $V_{b2} \neq 0$ V. In other words, the applied voltage is a negative voltage having an absolute value which is equal to or lower than 2.0 V. The applied voltage $V_{b2}$ is preferably −0.5 to −2.0 V, and more preferably −0.8 to −1.5 V. The applied voltage $V_{b2}$ may be maintained to be constant during step B2 or may be changed in a predetermined range. In addition, the applied voltage $V_{b2}$ may be equal to the applied voltage $V_{a1}$ or $V_{a3}$, or may be different from the applied voltage $V_{a1}$ or $V_{a3}$. However, since the oxide coating is removed in steps A1 and A3 once, it is preferable that an absolute value of the applied voltage $V_{b2}$ is equal to or smaller than the absolute value of the applied voltage $V_{a1}$ or $V_{a3}$.

The application of the applied voltage $V_{b2}$ makes it possible to remove the oxide coating formed on the surface of the detection electrode during step B1. When the absolute value of the applied voltage $V_{b2}$ is too small, it is not possible to remove the oxide coating from the surface of the detection electrode, and when the absolute value is too large, a problem arises in that the oxide coating is removed, then electrolysis occurs, and hydrogen gas or the like is generated.

The period of time $T_{b2}$, during which step B2 is performed, is equal to or shorter than the period of time $T_{a1}$, during which step A1 is performed. In addition, the period of time $T_{b2}$ is equal to or shorter than the period of time $T_{a3}$, during which step A3 is performed. Since the oxide coating is reliably removed in steps A1 and A3, it is possible to remove the coating to the extent that the measurement of the oxidation-reduction current is performed in step B3 without difficulty even in a short time. In addition, this is because the coating of benzotriazoles is likely to be formed when the period of time is long.

The period of time $T_{b2}$, during which step B2 is performed, is preferably 0.01 to 1.0 second, more preferably 0.01 to 0.5 seconds, and still more preferably 0.05 to 0.4 seconds. When the period of time $T_{b2}$ is equal to or longer than the preferable lower limit value (0.01 seconds), the oxide coating is likely to be removed. When the period of time $T_{b2}$ is equal to or shorter than the preferable upper limit value (1.0 second), the coating of benzotriazoles is unlikely to be formed.

Step B3 is continually performed after step B2. The applied voltage $V_{b3}$ of step B3 is −0.5 to 0.2 V, preferably −0.45 to 0.18 V, and more preferably −0.4 to 0.15 V.

The applied voltage $V_{b3}$ has to be maintained to be constant without change in step B3. This is because a measurement current is acquired in step B3.

The oxidation-reduction current is acquired as the measurement current in step B3. In the residual chlorine measuring apparatus according to the embodiment, the arithmetic controller 30 acquires, as the measurement current, the oxidation-reduction current measured by the ammeter of the potentiostat 20 in step B3.

The period of time Tb3, during which step B3 is performed, may be a predetermined period of time, or may be a period of time until the oxidation-reduction current measured by the ammeter of the potentiostat 20 is stabilized and acquisition of the measurement current is completed. Whether or not the oxidation-reduction current is stabilized can be determined by whether or not a fluctuation range in a predetermined period of time is equal to or narrower than a predetermined fluctuation range.

In a case where the period of time $T_{b3}$ is the predetermined period of time, the period of time $T_{b3}$ is preferably 0.01 to 3.0 seconds, more preferably 0.1 to 3.0 seconds, and still more preferably 0.1 to 2.0 seconds. When the period of time $T_{b3}$ is equal to or longer than the preferable lower limit value (0.01 seconds), the oxidation-reduction current is sufficiently stabilized. When the period of time $T_{b3}$ is equal to or shorter than the preferable upper limit value (3.0 second), it is possible to complete the measurement in a short time.

It is preferable that the acquisition of the measurement current in step B3 is performed in the latter half of step B3 in which the oxidation-reduction current is likely to be stabilized.

In addition, it is preferable that the acquisition of the measurement current is not performed only once, but is performed a plurality of times and an average thereof is obtained. For example, it is preferable that the measurement currents are acquired the plurality of times in the latter half of step B3 and are averaged. The obtaining of the average makes it possible to reduce variations in data.

Note that, in a case where the applied voltage $V_{b2}$ is equal to the applied voltage $V_{b3}$, or the like, and thus a timing of transition from step B2 to step B3 may not be clear, for the convenience of description, the start of acquiring the measurement current may be considered as the start of step B3.

In the method of measuring residual chlorine according to the embodiment, a total residual chlorine concentration (a total of a free residual chlorine concentration and a combined residual chlorine concentration) of the sample solution is calculated, according to the measurement current. Specifically, in a calibration curve obtained in advance, the total residual chlorine concentration corresponding to the measurement current is set to a total residual chlorine concentration of the sample solution.

The calibration curve is obtained by zero calibration using zero water and by span calibration using a span solution in which the total residual chlorine concentration is specified by a DPD method or the like. In other words, it is possible to create a calibration curve for each of the zero water and the span solution, by obtaining data of the total residual chlorine concentration and the measurement current.

Note that, the zero water is water from which residual chlorine is removed, for example, through leaving tap water as it is or processing tap water with activated carbon.

In the residual chlorine measuring apparatus according to the first embodiment, the arithmetic controller 30 is configured to store the calibration curve in advance. Otherwise, the arithmetic controller is configured to appropriately obtain the calibration curve by storing the data of the zero water and the span water used to create the calibration curve in advance. In this configuration, when the measurement current is acquired, the total residual chlorine concentration corresponding to the measurement current is obtained on the calibration curve stored in advance or the calibration curve obtained by the stored data, and the total residual chlorine concentration corresponding to the measurement current is output as the total residual chlorine concentration of the sample solution 41.

In the measurement step, step B1 to step B3 are repeated one or more times, preferably five times or less, more preferably twice to five times, and still more preferably three to four times. The repetitions performed too many times are not preferable because the oxide coating and the coating of benzotriazoles are accumulated each time of the repetition, and the accumulated coatings have a large effect on detection.

The measurement current is acquired whenever step B1 to step B3 are performed once. In a case where step B1 to step B3 are repeated a plurality of times, it is preferable that the total residual chlorine concentration is calculated using the average value of the measurement currents obtained every time the steps are repeated.

In addition, in a case where the total residual chlorine concentration is not calculated using the average but using the measurement current obtained any time, preferably, the total residual chlorine concentration is calculated using the measurement current obtained any time between the second to fifth times, and more preferably, the total residual chlorine concentration is calculated using the measurement current obtained any time between the third to fourth times.

As a result of the study of the inventors, when the preprocessing step is not performed, it is not possible to obtain a stable measurement current in the measurement step. In addition, although the preprocessing step is performed, it is difficult to perform the measurement in a case where the measurement step is not started immediately after the preprocessing step is ended. In other words, the preprocessing step needs to be performed so as to be continued from the preprocessing step.

In the residual chlorine measuring apparatus and the method of measuring residual chlorine according to the embodiment, since steps A1 to A3, which are performed for a relatively long time in the preprocessing step, it is possible to reliably remove the oxide coating and the coating of benzotriazoles. The oxide coating and the coating of benzotriazoles are formed again immediately after the removal. However, step B1 and step B2 are performed for a relatively short time in the measurement step, thereby it is possible to remove the oxide coating and the coating of benzotriazoles to the extent that the measurement current is acquired in step B3 without difficulty, and the measurement current according to the total residual chlorine concentration is considered to be obtained even in water in which benzotriazoles are present.

EXAMPLE

<Preparation of Sample Solution>

A sample solution used in the following example or experimental example was prepared by using the following reagent or undiluted solution.

Dechlorinated water: water obtained by volatilizing the chlorine content from tap water after the tap water was put in a constant temperature water tank at 25° C. and was stirred for 24 hours Activated-carbon filtered water: water obtained by performing a process using activated carbon on tap water Sodium hypochlorite stock solution: a sodium hypochlorite solution having a total residual chlorine concentration of approximately 12%

Sodium sulfamate (powder)

BTA stock solution: an aqueous solution of benzotriazole (chemical name: 1,2,3-benzotriazole) of 1,000 mg/L BTA diluted solution: a solution obtained by diluting the BTA stock solution using the dechlorinated water such that a concentration of benzotriazoles was 5 mg/L

[DBt-0]

Four types of sample solutions, which contained dichlorosulfamic acid at various concentrations, and did not contain benzotriazole, were prepared.

In other words, the sodium sulfamate and the sodium hypochlorite stock solution were dissolved in the dechlorinated water such that an effective chlorine concentration with respect to one mole of sodium sulfamate was 2 moles and the total residual chlorine concentration is approximately 8 mg/L, and then DBt-0 (8 mg/L) was obtained.

In addition, DBt-0 (8 mg/L) and the dechlorinated water were mixed at a volume ratio of 3:1 and DBt-0 (6 mg/L) having the total residual chlorine concentration of approximately 6 mg/L is obtained.

In addition, DBt-0 (having the total residual chlorine concentration of 8 mg/L) and the dechlorinated water were mixed at a volume ratio of 1:1 and DBt-0 (the total residual chlorine concentration of 4 mg/L) having the total residual chlorine concentration of approximately 4 mg/L was obtained.

Further, DBt-0 (8 mg/L) and the dechlorinated water were mixed at a volume ratio of 1:3 and DBt-0 (2 mg/L) having the total residual chlorine concentration of approximately 2 mg/L was obtained.

[MBt-0]

Four types of sample solutions, which contained monochlorosulfamic acid at various concentrations, and did not contain benzotriazole, were prepared.

In other words, the sodium sulfamate and the sodium hypochlorite stock solution were dissolved in the dechlorinated water such that the effective chlorine concentration with respect to one mole of sodium sulfamate was 1 mole and the total residual chlorine concentration is approximately 8 mg/L, and then MBt-0 (8 mg/L) was obtained.

In addition, MBt-0 (8 mg/L) and the dechlorinated water were mixed at a volume ratio of 3:1 and MBt-0 (6 mg/L) having the total residual chlorine concentration of approximately 6 mg/L was obtained.

In addition, MBt-0 (8 mg/L) and the dechlorinated water were mixed at a volume ratio of 1:1 and MBt-0 (4 mg/L) having the total residual chlorine concentration of approximately 4 mg/L was obtained.

Further, MBt-0 (8 mg/L) and the dechlorinated water were mixed at a volume ratio of 1:3 and MBt-0 (2 mg/L) having the total residual chlorine concentration of approximately 2 mg/L was obtained.

[DBt-5]

Four types of sample solutions, which contained dichlorosulfamic acid at various concentrations, and contained 5 mg/L of benzotriazole, were prepared.

In other words, the sodium sulfamate, the sodium hypochlorite stock solution, and a benzotriazole stock solution were dissolved in the dechlorinated water such that the effective chlorine concentration with respect to one mole of sodium sulfamate was 2 moles, the total residual chlorine concentration was approximately 8 mg/L, and a benzotriazole content was 5 mg/L, and then DBt-5 (8 mg/L) was obtained.

In addition, DBt-5 (8 mg/L) and the BTA diluted solution were mixed at a volume ratio of 3:1 and DBt-5 (6 mg/L) that had the total residual chlorine concentration of approximately 6 mg/L and had the benzotriazole content of 5 mg/L was obtained.

In addition, DBt-5 (8 mg/L) and the BTA diluted solution were mixed at a volume ratio of 1:1 and DBt-5 (4 mg/L) that had the total residual chlorine concentration of approximately 4 mg/L and had the benzotriazole content of 5 mg/L was obtained.

Further, DBt-5 (8 mg/L) and the BTA diluted solution were mixed at a volume ratio of 1:3 and DBt-5 (2 mg/L) that had the total residual chlorine concentration of approximately 2 mg/L and had the benzotriazole content of 5 mg/L was obtained.

[MBt-5]

Four types of sample solutions, which contained monochlorosulfamic acid at various concentrations, and contained 5 mg/L of benzotriazoles, were prepared.

In other words, the sodium sulfamate, the sodium hypochlorite stock solution, and the benzotriazole stock solution were dissolved in the dechlorinated water such that the effective chlorine concentration with respect to one mole of sodium sulfamate was 1 mole, the total residual chlorine concentration was approximately 8 mg/L, and the benzotriazole content was 5 mg/L, and then MBt-5 (8 mg/L) was obtained.

In addition, MBt-5 (8 mg/L) and the BTA diluted solution were mixed at a volume ratio of 3:1 and MBt-5 (6 mg/L) that had the total residual chlorine concentration of approximately 6 mg/L and had the benzotriazole content of 5 mg/L was obtained.

In addition, M Bt-5 (8 mg/L) and the BTA diluted solution were mixed at a volume ratio of 1:1 and MBt-5 (4 mg/L) that had the total residual chlorine concentration of approximately 4 mg/L and had the benzotriazole content of 5 mg/L was obtained.

Further, MBt-5 (8 mg/L) and the BTA diluted solution were mixed at a volume ratio of 1:3 and MBt-5 (2 mg/L) that had the total residual chlorine concentration of approximately 2 mg/L and had the benzotriazole content of 5 mg/L was obtained.

[DBt-2 (8 mg/L)]

A sample solution, which contained dichlorosulfamic acid so as to have the total residual chlorine concentration of approximately 8 mg/L and contained 2 mg/L of benzotriazole, was prepared.

In other words, the sodium sulfamate, the sodium hypochlorite stock solution, and the benzotriazole stock solution were dissolved in the dechlorinated water such that the effective chlorine concentration with respect to one mole of sodium sulfamate was 2 moles, the total residual chlorine concentration was approximately 8 mg/L, and the benzotriazole content was 2 mg/L, and then DBt-2 (8 mg/L) was obtained.

[DBt-0.5 (8 mg/L)]

A sample solution, which contained dichlorosulfamic acid so as to have the total residual chlorine concentration of approximately 8 mg/L and contained 0.5 mg/L of benzotriazole, was prepared.

In other words, the sodium sulfamate, the sodium hypochlorite stock solution, and the benzotriazole stock solution were dissolved in the dechlorinated water such that the effective chlorine concentration with respect to one mole of sodium sulfamate was 2 moles, the total residual chlorine concentration was approximately 8 mg/L, and the benzotriazole content was 0.5 mg/L, and then DBt-0.5 (8 mg/L) was obtained.

<Measurement of Total Residual Chlorine Concentration>

The total residual chlorine concentration of the sample solutions was calculated in accordance with an "iodometric titration method" (hereinafter, referred to as a "DPD method") described in (14) standard chlorine water of "absorptiometric method using 30.3 diethyl-p-phenylenediamine" in 2011 edition of a drinking water test Method. Specifically, measurement was performed as follows.

(a) Preparation of DPD Reagent 1.0 g of N,N-diethyl-phenylenediamine sulfate and 24 g of anhydrous sodium sulfate were mixed and the DPD (N,N-diethyl-p-phenylenediamine) reagent was prepared.

(b) Preparation of Phosphate Buffer Solution (pH=6.5)

35.4 mL of a 0.2 mol/L sodium hydroxide solution was added to 100 mL of 0.2 mol/L potassium dihydrogen phosphate and a mixed solution of potassium dihydrogen phosphate and sodium hydroxide solution was obtained. 0.13 g of trans-1,2-cyclohexanediaminetetraacetic acetic hydrate was dissolved in the mixed solution of potassium dihydrogen phosphate and sodium hydroxide solution, and phosphate buffer solution (pH=6.5) was prepared.

(c) Measurement of Total Residual Chlorine Concentration 2.5 mL of phosphate buffer solution was put in a stoppered container having a volume of 50 mL, then, 0.5 g of the DPD reagent was added to the phosphate buffer solution in the container, then, the sample solution and ion-exchanged water were added so as to obtain a total amount of 50 mL, and mixing was performed.

Approximately 0.5 g of potassium iodide was added and dissolved in 50 mL of the obtained mixed solution. Next, 3 mL of the solution obtained after the addition of the potassium iodide was put in an absorption cell, absorbance of a wave length of 528 nm was measured using a photoelectric spectrophotometer after two minutes after the addition of the potassium iodide, and the total residual chlorine concentration was calculated using the calibration curve created in advance.

Example

The method of measuring residual chlorine according to the second embodiment was performed on the sample solutions as the target, using the residual chlorine measuring apparatus according to the first embodiment.

A sensor including the detection electrode 11 that had a gold electrode with a size of 0.1×3 mm and the silver/silver chloride counter electrode 12 was used as the sensor 10.

Figure 2:
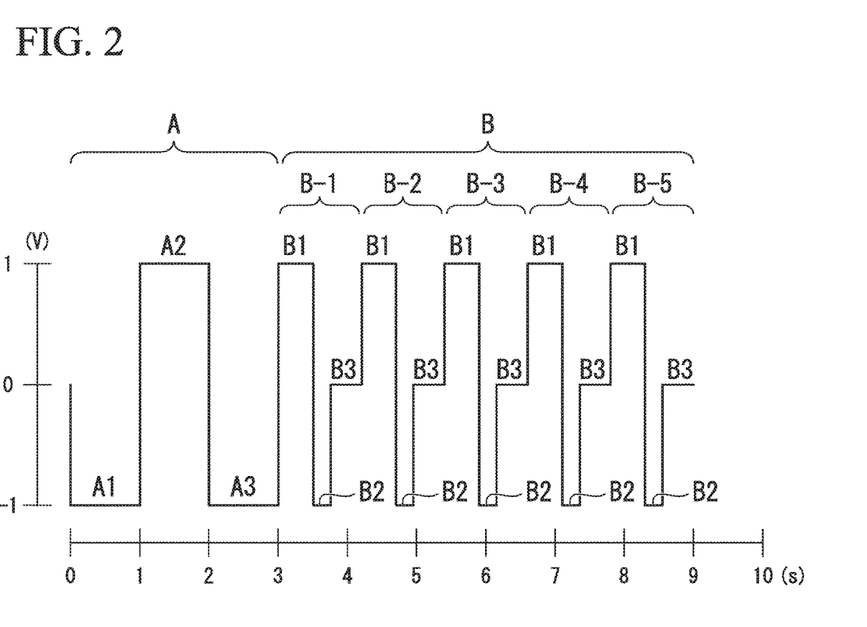
FIG. 2 is a diagram showing applied voltages in preprocessing steps and in measurement steps of the method of measuring residual chlorine according to an example of the present invention.

As shown in FIG. 2, the preprocessing step A was a step in which, after step A1 satisfying the following conditions was performed, step A2 and step A3 which satisfied the following conditions were continually performed once.

Step A1: a step of applying the applied voltage $V_{a1}=-1$ V for one second.

Step A2: a step of applying the applied voltage $V_{a2}=1$ V for one second.

Step A3: a step of continually applying the applied voltage $V_{a3}=-1$ V for one second, after step A2.

In addition, the measurement step B was a step of repeating step B1 to step B3 which satisfied the following conditions five times of B-1 to B-5. In addition, for 0.25 to 0.50 seconds after the start of step B3, the oxidation-reduction currents were acquired 50 times per 5 mS and an average of the acquired oxidation-reduction currents was obtained as the measurement current.

Step B1: a step of applying the applied voltage $V_{b1}=1$ V for 0.5 seconds.

Step B2: a step of continually applying the applied voltage $V_{b2}=-1$ V for 0.2 seconds, after step B1.

Step B3: a step of continually applying the applied voltage $V_{b3}=0$ V for 0.5 seconds, after step B2.

FIGS. 3 to 7 show results of the method of measuring residual chlorine according to the second embodiment performed on, as the sample solution, four types of DBt-0 (2 mg/L) to DBt-0 (8 mg/L), four types of DBt-5 (2 mg/L) to DBt-5 (8 mg/L), four types of MBt-0 (2 mg/L) to MBt-0 (8 mg/L), four types of MBt-5 (2 mg/L) to MBt-5 (8 mg/L), the dechlorinated water, and the BTA diluted solution.

Note that, in FIGS. 3 to 7, data of the total residual chlorine concentration of 0 mg/L is the data of the dechlorinated water or the BTA diluted solution as the sample solution.

In addition, in FIGS. 3 to 7, data of the total residual chlorine concentration of approximately 2 mg/L, approximately 4 mg/L, approximately 6 mg/L, approximately 8 mg/L, is data of DBt-0 (plots of white diamonds) having, as the sample solution, four types of DBt-0 solutions (DBt-0 (2 mg/L) to DBt-0 (8 mg/L)) and data of DBt-5 (plots of black triangles) having, as the sample solution, four types of DBt-5 solutions (DBt-5 (2 mg/L) to DBt-5 (8 mg/L)). In addition, in FIGS. 3 to 7, data of the total residual chlorine concentration is data of MBt-0 (plots of white squares) having, as the sample solution, four types of MBt-0 solutions (MBt-0 (2 mg/L) to MBt-0 (8 mg/L)) and data of MBt-5 (plots of black circles) having, as the sample solution, four types of MBt-5 solutions (MBt-5 (2 mg/L) to MBt-5 (8 mg/L)).

Figure 3:
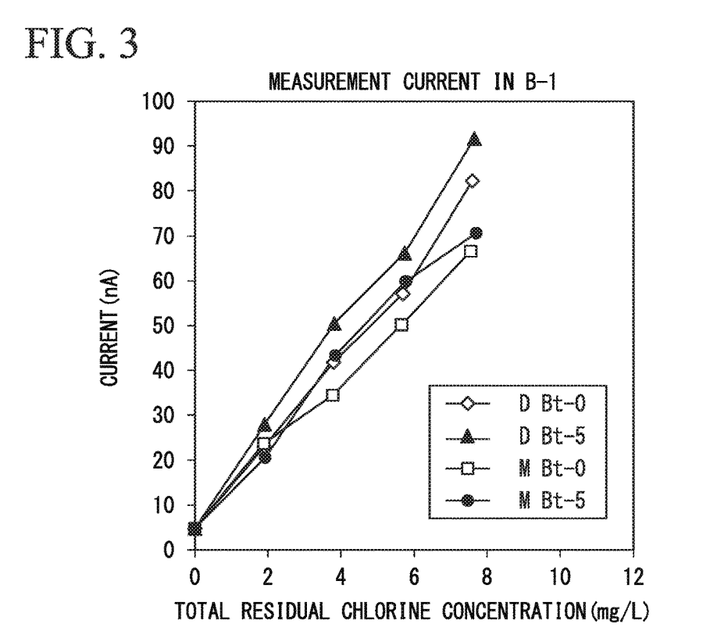
FIG. 3 is a graph showing a relationship between a current value obtained in a measurement step and a total residual chlorine concentration.
Figure 4:
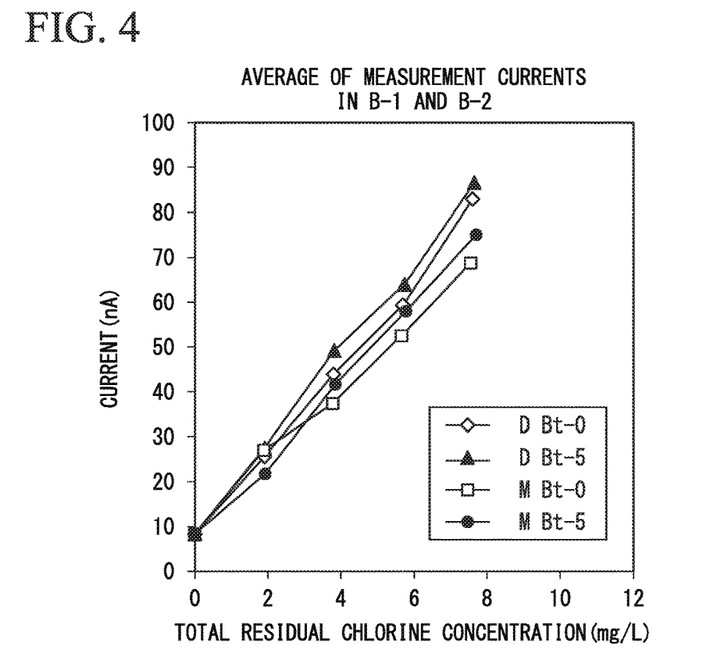
FIG. 4 is a graph showing a relationship between a current value obtained in a measurement step and a total residual chlorine concentration.
Figure 5:
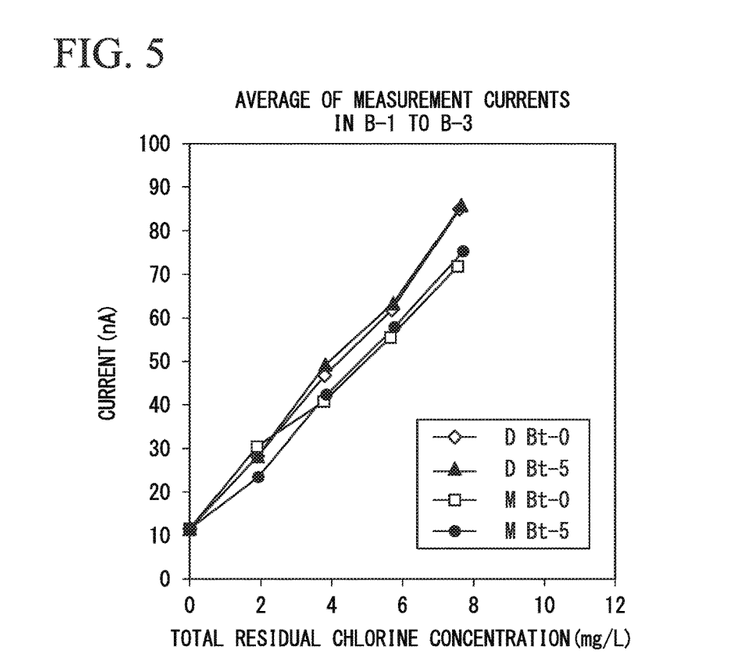
FIG. 5 is a graph showing a relationship between a current value obtained in a measurement step and a total residual chlorine concentration.
Figure 6:
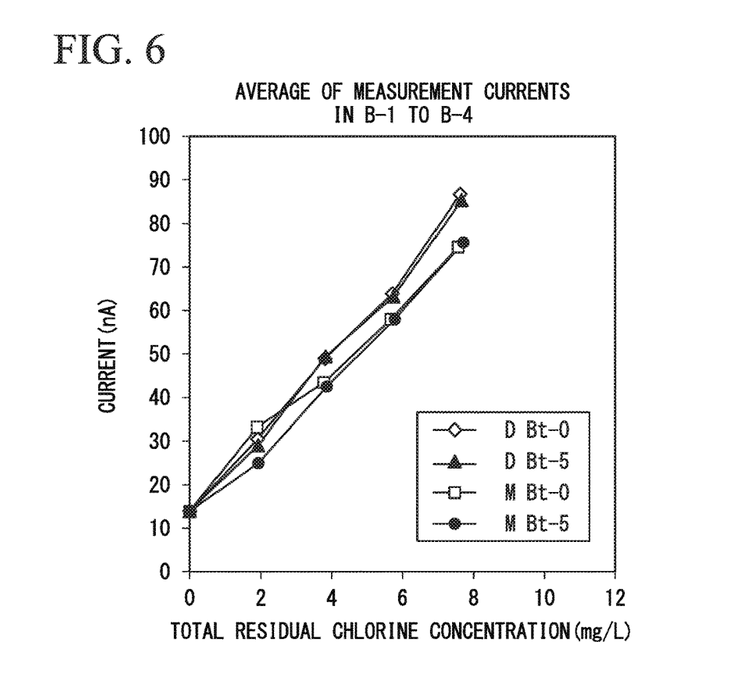
FIG. 6 is a graph showing a relationship between a current value obtained in a measurement step and a total residual chlorine concentration.
Figure 7:
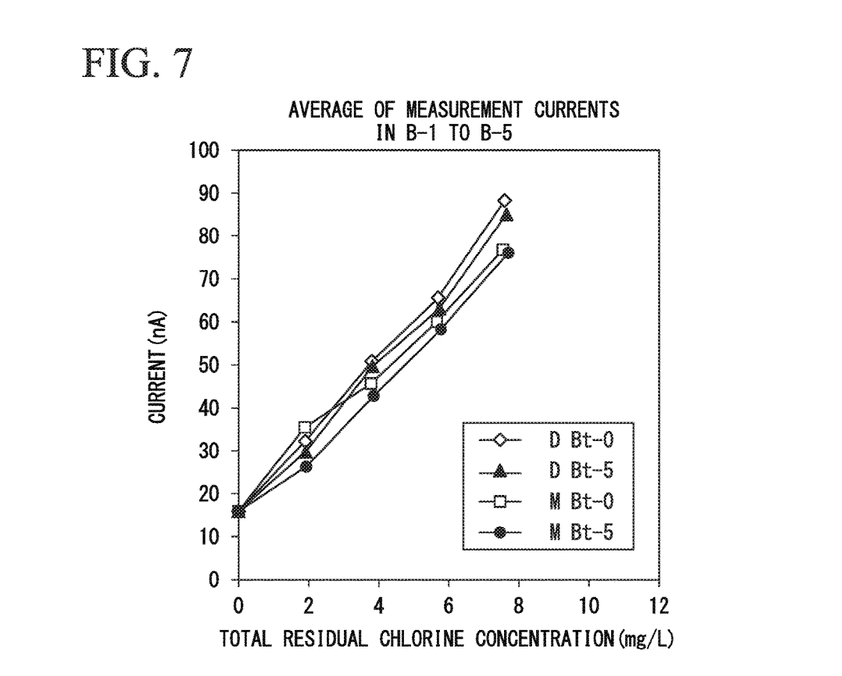
FIG. 7 is a graph showing a relationship between a current value obtained in a measurement step and a total residual chlorine concentration.

FIG. 3 shows the measurement currents of the sample solutions obtained in B-1. In addition, FIG. 4 shows average values of the measurement currents obtained in B-1 and the measurement currents obtained in B-2. In addition, FIG. 5 shows average values of the measurement currents obtained in B-1, the measurement currents obtained in B-2 and the measurement currents obtained in B-3. In addition, FIG. 6 shows average values of the measurement currents obtained in B-1 to the measurement currents obtained in B-4. In addition, FIG. 7 shows average values of the measurement currents obtained in B-1 to the measurement currents obtained in B-5.

As shown in FIGS. 3 to 7, according to the method of measuring residual chlorine according to the second embodiment, it is found that the sufficient measurement currents are obtained in the case where benzotriazole is contained.

In addition, in the case of the monochlorosulfamic acid solution and the dichlorosulfamic acid, it is found that there is no significant difference in the measurement current.

In addition, when the measurement steps of step B1 to step B3 are repeated a plurality of times and the obtained measurement currents are averaged, it is found that benzotriazole has a small influence on the measurement current. Particularly, as shown in FIGS. 5 and 6, when the measurement currents obtained during repetition of the measurement steps three to four times are averaged, it is found that benzotriazole has a very small influence on the measurement current. As shown in FIG. 7, when the measurement currents obtained during repetition of the measurement steps five times are averaged, it is found that benzotriazole has a slight influence on the measurement current. This is considered to be because the oxide coating and the coating of benzotriazoles are formed to the B-4 step are accumulated in the B-5 step.

Experimental Example

Figure 8:
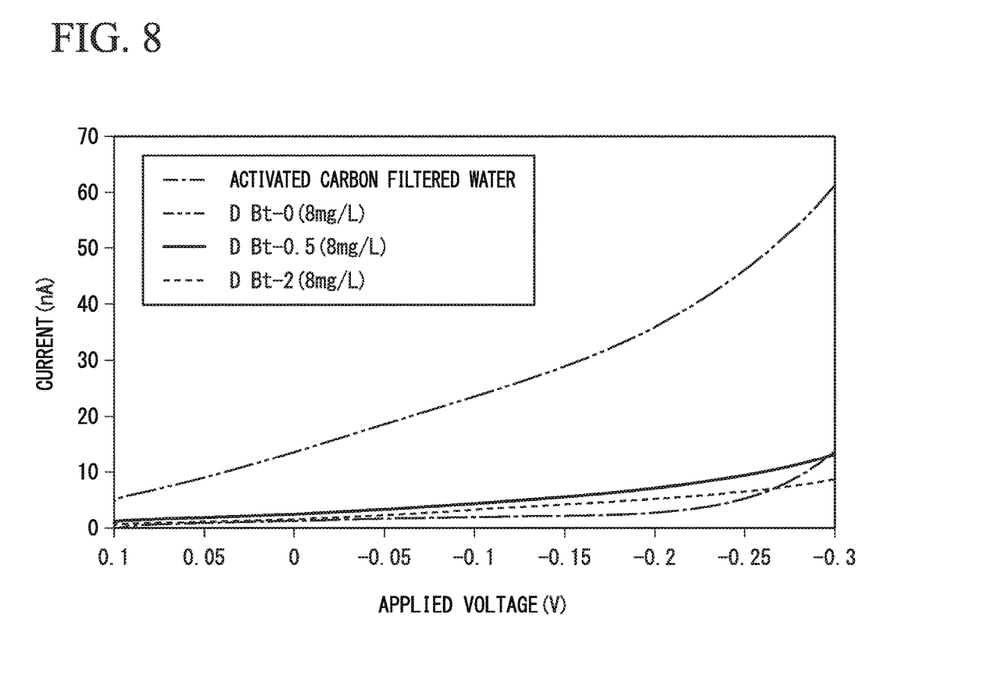
FIG. 8 is a graph showing data obtained by studying an influence of benzotriazole on a polarogram showing a relationship between an applied voltage and an oxidation-reduction current.

Polarogram showing a relationship between the applied voltage and the oxidation-reduction current of, as the sample solution, the activated carbon filtered water, DBt-0 (8 mg/L), DBt-0.5 (8 mg/L), and DBt-2 (8 mg/L) was examined. A sweep rate of the applied voltage was 50 mV/min. A gold electrode having a diameter of 2 mm was used as the detection electrode, and rotation was applied to the extent that a linear velocity of approximately 100 cm/s was obtained. The counter electrode was made of silver/silver chloride.

A result thereof is shown in FIG. 8. As shown in FIG. 8, when the method according to the second embodiment is not used, the oxidation-reduction current corresponding to the residual chlorine concentration is very small when the amount of benzotriazole is only by 0.5 mg/L. Thus, when the amount of benzotriazole is only 2 mg/L, it is found that the current at the applied voltage of 0 V is almost equal to a current of the activated carbon filtered water.

According to the residual chlorine measuring apparatus and the method of measuring residual chlorine according to the embodiments, it is possible to measure the total residual chlorine concentration of water containing hypochlorous acid or a hypochlorite, and sulfamic acid or a sulfamic acid salt, such as cooling water, pulp and paper process water, dust collecting water, scrubber water, or fountain, regardless of the containing of benzotriazole or a benzotriazole salt.

While preferred embodiments of the invention have been described and shown above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. A residual chlorine measuring apparatus comprising:
   a detection electrode that is immersed in a sample solution containing one selected from the group consisting of benzotriazole and benzotriazole salt, the detection electrode being made of gold or platinum;
   a counter electrode that is immersed in the sample solution, the counter electrode being made of silver/silver chloride;
   a voltage applying device that applies an applied voltage between the detection electrode and the counter electrode;
   an ammeter that measures an oxidation-reduction current flowing between the detection electrode and the counter electrode; and
   an arithmetic controller that controls the voltage applying device, acquires the oxidation-reduction current measured by the ammeter, and stores the oxidation-reduction current,
   wherein the arithmetic controller is configured to perform
      a step A1 of applying an applied voltage $V_{a1}$ in a range of −0.5 to −2.0 V between the detection electrode and the counter electrode for a period of time $T_{a1}$,
      a step A2 of applying an applied voltage $V_{a2}$ in a range of 0.5 to 2.0 V between the detection electrode and the counter electrode for a period of time $T_{a2}$,
      a step A3 of applying an applied voltage $V_{a3}$ in a range of −0.5 to −2.0 V, after the step A2, between the detection electrode and the counter electrode for a period of time $T_{a3}$,
      a step B1 of applying an applied voltage $V_{b1}$ in a range of 0.5 to 2.0 V between the detection electrode and the counter electrode for a period of time $T_{b1}$ that satisfies a condition of $T_{b1} \leq T_{a2}$,
      a step B2 of applying an applied voltage $V_{b2}$ that satisfies conditions of $V_{b2} = 0$ to −2.0 V and $V_{b2} \neq 0$ V, after the step B1, between the detection electrode and the counter electrode for a period of time $T_{b2}$ that satisfies conditions of $T_{b2} \leq T_{a1}$ and $T_{b2} \leq T_{a3}$, and
      a step B3 of applying an applied voltage $V_{b3}$ in a range of −0.5 to 0.2 V, after the step B2, between the detection electrode and the counter electrode while a voltage is maintained to be constant,
   wherein:
   the arithmetic controller is configured to control the voltage applying device such that the voltage applying device performs the step A2 and the step A3 one or more times after the step A1 as a preprocessing step to remove an oxide coating made from said one selected from the group consisting of benzotriazole and benzotriazole salt which are formed on the detection electrode,
   the arithmetic controller is configured to control the voltage applying devices such that step B1 to the step B3 are performed one or more times after performing the step A2 and the step A3 one or more times, and
   the arithmetic controller is configured to acquire an oxidation-reduction current obtained by the ammeter in the step B3 as a measurement current, and to calculate a total residual chlorine concentration of the sample solution, according to the measurement current,
   the arithmetic controller is configured to control an absolute value of the applied voltage $V_{b2}$ to be equal to or smaller than an absolute value of the applied voltage $V_{a1}$, and
   the arithmetic controller is configured to control the absolute value of the applied voltage $V_{b2}$ to be equal to or smaller than an absolute value of the applied voltage $V_{a3}$.

2. The residual chlorine measuring apparatus according to claim 1,
   wherein the period of time $T_{a1}$ is 0.1 to 3.0 seconds, the period of time $T_{a2}$ is 0.1 to 3.0 seconds, the period of time $T_{a3}$ is 0.1 to 3.0 seconds, the period of time $T_{b1}$ is 0.01 to 1.0 second, and the period of time $T_{b2}$ is 0.01 to 1.0 second.

3. The residual chlorine measuring apparatus according to claim 1, wherein the absolute value of the applied voltage $V_{a3}$ is preferably equal to or smaller than the absolute value of the applied voltage $V_{a1}$.

4. The residual chlorine measuring apparatus according to claim 1, wherein an absolute value of the applied voltage $V_{b1}$ is equal to or smaller than an absolute value of the applied voltage $V_{a2}$.

* * * * *